(12) United States Patent
Horowitz

(10) Patent No.: US 6,340,580 B1
(45) Date of Patent: Jan. 22, 2002

(54) METHODS FOR PURIFYING POLYHYDROXY ALKANOATES

(75) Inventor: Daniel Horowitz, Somerville, MA (US)

(73) Assignee: Metabolix, Inc., Cambridge, MA (US)

( * ) Notice: Subject to any disclaimer, the term of this patent is extended or adjusted under 35 U.S.C. 154(b) by 0 days.

(21) Appl. No.: 09/570,261

(22) Filed: May 12, 2000

Related U.S. Application Data

(60) Provisional application No. 60/133,747, filed on May 12, 1999.

(51) Int. Cl.$^7$ .............................. C12P 7/42; C08G 63/06; C08G 63/08
(52) U.S. Cl. .................. 435/135; 435/146; 435/243; 435/261; 528/354; 528/361; 528/493; 528/502 A
(58) Field of Search ................................ 435/135, 146, 435/243, 261; 528/354, 361, 502 A, 493

(56) References Cited

U.S. PATENT DOCUMENTS

| | | | | |
|---|---|---|---|---|
| 4,336,334 A | * | 6/1982 | Powell et al. | 435/146 |
| 4,705,604 A | * | 11/1987 | Vanlautem et al. | 435/135 |
| 5,364,778 A | * | 11/1994 | Byrom | 435/135 |
| 5,552,515 A | * | 9/1996 | Hubbs et al. | 528/354 |
| 5,610,041 A | * | 3/1997 | Somerville et al. | 435/135 |
| 5,625,029 A | * | 4/1997 | Hubbs et al. | 528/354 |
| 5,942,597 A | * | 8/1999 | Noda et al. | 528/361 |
| 6,043,063 A | * | 3/2000 | Kurdikar et al. | 435/135 |
| 6,087,471 A | * | 7/2000 | Kurdikar et al. | 528/480 |
| 6,248,862 B1 | * | 6/2001 | Asrar et al. | 528/361 |

* cited by examiner

*Primary Examiner*—Herbert J. Lilling
(74) *Attorney, Agent, or Firm*—Holland & Knight LLP

(57) ABSTRACT

A method is provided for isolating and purifying PHA from microbial or plant biomass that contains PHA. The method includes the step of extracting PHA from the biomass using at least one solvent while simultaneously subjecting the biomass to a filtration process to remove cells. In a preferred embodiment of the method, an aqueous slurry of the biomass is directly extracted by diafiltration using an organic solvent. In a preferred diafiltration process, an aqueous slurry of microbial cells comprising PHA is recirculated through a filtration membrane, wherein the membrane has a pore size sufficiently small to reject individual cells or such aggregates of cells as may exist in the slurry. As liquid is progressively removed from the biomass slurry (by flowing out from the filtration membrane), an organic solvent, preferably a water-miscible solvent that also is a solvent for the PHA, is added to the biomass slurry at a rate which approximates the rate of liquid permeation through the filter, thereby maintaining the volume of the biomass slurry. Impurities which are insoluble in water become dissolved in the solvent-water mixture and pass through the filter membrane, and when the organic solvent concentration reaches a certain level, the PHA becomes soluble and flows through the filtration membrane and can be desolventized to recover the polymer.

13 Claims, No Drawings

METHODS FOR PURIFYING POLYHYDROXY ALKANOATES

CROSS-REFERENCE TO RELATED APPLICATIONS

Priority is claimed to U.S. Ser. No. 60/133,747, filed May 12, 1999.

BACKGROUND OF THE INVENTION

The present invention generally relates to methods for recovering polyhydroxyalkanoates ("PHAs") from microbial or plant biomass. An improved understanding of the PHA biosynthetic pathways has allowed for the use of microbial organisms, both natural and recombinant, as well as plant cells, to produce significant quantities of PHA. However, difficulties remain in developing efficient and cost-effective recovery of the PHA at a useful levels of quality and purity from these biological source materials. Previous methods for isolating and purifying PHAs from biomass have included, for example, aqueous routes as well as organic solvent routes.

For example, U.S. Pat. No. 5,364,778 to Byrom discloses an aqueous method wherein biomass comprising PHA is maintained as an aqueous slurry in which the PHA is generally insoluble. The slurry is subjected to various treatments designed to digest, degrade, or otherwise make water-soluble the non-PHA biomass. This solubilized biomass then is removed from the slurry by centrifugation, filtration, or other means. Aqueous-based routes, however, generally have certain disadvantages, particularly which applied to large scale processing. Examples of these disadvantages include (a) effective purification is made more difficult because many impurities, including some surfactants useful for the solubilizing treatments, may be tightly adsorbed to the surface of the PHA particles; (b) many volumes (i.e. large quantities) of wash water may be required by the process, creating used wash water and its attendant disposal difficulties; (c) multiple solubilizing treatments may be required to obtain high purity PHA; (d) drying of the water-based PHA slurry may be time-consuming and costly; (e) PHA particles may cause extensive fouling of filtration membranes, centrifuges, and other process equipment; and (f) solubilizing treatments may require expensive reagents and lengthy process times and/or high temperatures to be effective.

Examples of organic solvent-based methods processes are disclosed in U.S. Pat. No. 4,101,533 to Lafferty et al. and U.S. Pat. No. 5,422,257 to Ohleyer. In these methods, an organic solvent for the PHA contained in a biomass is mixed with the biomass, resulting in the dissolution of the PHA. The organic solution comprising the PHA then is separated from the remaining insoluble biomass by filtration, centrifugation, or other means. The organic solution then is desolventized to recover the PHA. These organic solvent routes suffer disadvantages similar to the disadvantages associated with aqueous routes, including (a) a relatively large volume of solvent is required to completely extract the PHA from biomass; (b) biomass may need to dried prior to solvent extraction, which may be costly and time-consuming; and (c) solvents may co-extract impurities along with the PHA, such as lipids or other hydrophobic biological materials, necessitating further processing of the extract to obtain PHA of satisfactory purity. It would be advantageous to develop improved, more cost-effective processes for recovering PHA from PHA-containing biomass.

It is therefore an object of this invention to provide a method of recovering PHA from PHA-containing biomass using a process that is more simple, relatively faster, uses aqueous and/or organic solvents more efficiently, and possibly yields a more pure PHA product than conventional processes.

It is another object of the present invention to provide a method of recovering PHA from PHA-containing biomass using a process that can be employed economically in a commercial-scale production process.

SUMMARY OF THE INVENTION

A method is provided for isolating and purifying PHA from biomass which comprises PHA. The method includes the step of extracting PHA from the biomass using at least one solvent while simultaneously subjecting the biomass to a filtration process to remove cells. In a preferred embodiment of the method, biomass comprising PHA (for example an aqueous slurry of microbial cells obtained from a fermentation process) is directly extracted by diafiltration sing an organic solvent, to obtain PHA.

In a preferred diafiltration process, an aqueous slurry of microbial cells comprising PHA is recirculated through a filtration membrane, wherein the membrane has a pore size sufficiently small to reject individual cells or such aggregates of cells as may exist in the slurry. An outflow of liquid from the filtration membrane occurs under conditions where a pressure drop exists across the filtration membrane. As the liquid is progressively removed from the biomass slurry, an organic solvent, preferably a water-miscible solvent that also is a solvent for the PHA, is added to the biomass slurry. The solvent addition should be made at a rate which approximates the rate of liquid permeation through the filter in order to maintain the volume of the biomass slurry. As the concentration of organic solvent in the slurry increases, various impurities which are insoluble in water become dissolved in the solvent-water mixture and pass through the filter membrane. When the organic solvent concentration reaches a certain level, the PHA becomes soluble and flows through the filtration membrane. The filtrate comprising PHA then is desolventized to recover the polymer.

The method has the advantages that (a) it is not generally necessary to dry the biomass prior to solvent extraction; (b) it is readily possible to fractionate the PHA from other impurities to obtain relatively pure PHA in a single process, because the biomass is subjected to a gradient in solvent concentration; (c) the entire process of extracting and purifying PHA from biomass can be accomplished using a minimum of process stages and equipment; and (d) the method efficiently uses solvents, especially when the biomass slurry is relatively concentrated and when the diafiltration is conducted at a constant volume diafiltration. Furthermore, by using volatile organic solvents, it is relatively easy to desolventize the PHA solutions and to recover and reuse the solvent from the filtrates generated in the diafiltration process.

DETAILED DESCRIPTION OF THE INVENTION

A method has been developed for isolating and purifying polyhydroxyalkanoates ("PHAs")from biomass comprising PHAs. The method includes the step of extracting PHA from the biomass using at least one solvent while simultaneously subjecting the biomass to a filtration process to remove cells.

1. The PHA-Containing Biomass

The biomass materials are derived from PHA-producing plants or PHA producing microorganisms.

Polymer Compositions

As used herein, "polyhydroxyalkanoate" and "PHA" refer to polymers that contain one or more units, for example between 10 and 100,000, and preferably between 100 and 30,000 units of the following formula I:

—OCR$^1$R$^2$(CR$^3$R$^4$)$_n$CO—;

wherein n is an integer, for example between 1 and 15, and in a preferred embodiment, between 1 and 4; and wherein R$^1$, $^2$, R$^3$, and R$^4$ independently can be hydrocarbon radicals including long chain hydrocarbon radicals; halo- and hydroxy-substituted radicals; hydroxy radicals; halogen radicals; nitrogen-substituted radicals; oxygen-substituted radicals; and/or hydrogen atoms.

As used herein, the formula —(CR$^3$R$^4$)$_n$— is defined as including the following formulas:

—CR$^3$R$^4$—(where n=1);

—CR$^3$R$^4$CR$^3'$R$^4'$—(where n=2); and

—CR$^3$R$^4$CR$^3'$R$^4'$CR$^{3''}$R$^{4''}$—(where n=3);

wherein R$^3$, R$^4$, R$^{3'}$, R$^{4'}$, R$^{3''}$, and R$^{4''}$, can be independently hydrocarbon radicals including long chain hydrocarbon radicals; halo- and hydroxy-substituted radicals; hydroxy radicals; halogen radicals; nitrogen-substituted radicals; oxygen-substituted radicals; and/ or hydrogen atoms. Thus, formula I includes units derived from 2-hydroxyacids (n=0), 3-hydroxyacids (n=1),4-hydroxyacids (n=2), and 5-hydroxyacids (n=3), and 6-hydroxyacids (n=4).

These units may be the same in a homopolymer, or be more different units, as for example in a copolymer or terpolymer. The polymers typically have a molecular weight over 300, for example between 300 and 10$^7$, and in a preferred embodiment 10,000 to 10,000,000 Daltons.

Preferred PHAs include poly-3-hydroxyoctanoate (PHO) or other microbial polyesters comprising hydroxyacids from C6 to C14 hydroxyacids. Other preferred polymers include poly-3-hydroxybutyrate-co-3-hydroxyvalerate, poly-3-hydroxybutyrate-co-3-hydroxypropionate, poly-3-hydroxybutyrate-co-4-hydroxybutyrate, poly-3-hydroxybutyrate-co-4-hydroxyvalerate, poly-3-hydroxybutyrate-co-3-hydroxyhexanoate, poly-3-hydroxybutyrate-co-3-hydroxyoctanoate, poly-4-hydroxybutyrate, poly-3-hydroxypropionate, poly-4-hydroxyvalerate.

Sources of PHA-Containing Biomass

The PHA biomass is typically generated from a fermentation process (wherein the biological source is a microorganism which naturally produces the PHAs or which can be induced to produce the PHAs by manipulation of culture conditions and feedstocks, or microorganisms) or produced in a plant, or plant part, which has been genetically engineered so that it produces PHAs.

(i) Microbial Sources

Methods which can be used for producing PHA polymers from microorganisms which naturally produce polyhydroxyalkanoates are described in U.S. Pat. No. 4,910,145 to Holmes, et al.; Braunegg et. al., J. Biotechnology 65:127–161 (1998).

Methods for producing PHAs in natural or genetically engineered organisms are described in Madison & Huisman, Microbiol. Mol. Biol. Rev. 63:1–53 (1999); Choi & Lee, Appl. Microbiol. Biotechnol. 51:13–21 (1999); Witholt & Kessler, Current Opinion in Biotechnology 10:279–285 (1999); Williams & Peoples, CHEMTECH, 26:38–44 (1996); U.S. Pat. Nos. 5,245,023; 5,250,430; 5,480,794; 5,512,669; 5,534,432 to Peoples and Sinskey; and U.S. Pat. No. 5,563,239 to Hubbs et al. U.S. Pat. No. 5,292,860 to Shiotani et al. describes the manufacture of the PHA copolymer poly(3-hydroxybutyrate-co-3-hydroxyhexanoate. U.S. Pat. No. 5,871,890 to Naylor describes the manufacture of PHAs by fermenting Alcaligenes eutrophus on vegetable oil feedstocks.

(ii) Plant Sources

PHA can be recovered from essentially any plant type, including transgenic plants which offers many advantages for the production of PHAs. Transgenic crop plants for production of PHAs can be obtained using methods available in the art. (U.S. Pat. Nos. 5,245,023 and 5,250,430; 5,502,273; 5,534,432; 5,602,321; 5,610,041; PCT WO, 9100917, WO 9219747, WO 9302187, WO 9302194 and WO 9412014; Poirier et al., 1992 Science 256:520–23, van der Leij & Witholt, 1995, Can. J. Microbiol. 41 (supp):222–38; Nawrath & Poirier, 1996, presented at The International Symposium on Bacterial Polyhydroxyalkanoates, Eggink et al., eds. Davos Switzerland, August 18–23; Williams & Peoples, 1996, CHEMTECH 26:38–44). Transgenic plant crop production can produce PHA polymers at both a price and a scale that is competitive with petrochemical derived plastics. Transgenic plant derived PHA polymers or their derivatives can be processed and separated from plant biomass in commercially useful forms. The location of the PHA in the plant crop can be varied to maximize the yield of PHA from the plant. For example, the plants can be monocots or dicots and suitable plant source materials can be derived from roots, stems, leaves, flowers, fruits, and seeds.

PHAs can be isolated from plant biomass derived from plants such as soybean, cotton, coconuts, groundnuts, rapeseed, sunflower seed, olive, palm, sesame seed, linseed, castor, safflower seed, tobacco, sugarcane, switchgrass, and potato. In addition to the PHA polymers, the plant oil in seed crop plants can be isolated and recovered during the processing, as described in PCT WO 97/15681 to Metabolix, Inc. and U.S. Ser. No. 08/548,840, which is incorporated by reference herein. The methods for processing the plant biomass can be tailored based on the properties of the particular PHA polymer or derivative being isolated, and based on the type of plant crop and the plant components being extracted.

III. Process for PHA Recovery from Biomass

The method includes the step of extracting PHA from the biomass using at least one solvent while simultaneously subjecting the biomass to a filtration process to remove cells.

Diafiltration

In a preferred embodiment of the method, biomass comprising PHA (for example an aqueous slurry of microbial cells obtained from a fermentation process) is directly extracted by modification of a typical diafiltration process in which an organic solvent is used instead of an aqueous diluent. Standard diafiltration processes are well known in the art and are described for example by Zeman & Zydney, Microfiltration and Ultrafiltration Principles and Applications, Marcel Dekker, Inc. New York, N.Y. pp. 391–96 (1996). During this modified process, as the concentration of organic solvent increases, the PHA is solubilized and appears in the eluant which is collected. The PHA is then recovered from the eluant by standard procedures including precipitation in a non-solvent, solvent evaporation or stripping to recover the PHA. The solvent containing eluant is retained and the solvent recovered by distillation or other techniques well known in the art.

In a preferred embodiment of the method, biomass comprising PHA (for example an aqueous slurry of microbial cells obtained from a fermentation process) is directly extracted by diafiltration using an organic solvent, to obtain PHA.

The method has the advantages that (a) it is not generally necessary to dry the biomass prior to solvent extraction; (b) it is readily possible to fractionate the PHA from other impurities to obtain relatively pure PHA in a single process, because the biomass is subjected to a gradient in solvent concentration; (c) the entire process of extracting and purifying PHA from biomass can be accomplished using a minimum of process stages and equipment; and (d) the method efficiently uses solvents, especially when the biomass slurry is relatively concentrated and when the diafiltration is conducted at a constant slurry volume ("constant volume diafiltration"). Furthermore, by using volatile organic solvents, it is relatively easy to desolventize the PHA solutions and to recover and reuse the solvent from the filtrates generated in the diafiltration process.

In a preferred diafiltration process, an aqueous slurry of microbial cells comprising PHA is recirculated through a filtration membrane, wherein the membrane has a pore size sufficiently small to reject individual cells or such aggregates of cells as may exist in the slurry. An outflow of liquid, the eluant which can be an aqueous solution, an aqueous solution/miscible solvent mixture, or solvent, from the filtration membrane occurs under conditions where a pressure drop exists across the filtration membrane. As the liquid is progressively removed from the biomass slurry, an organic solvent, preferably a water-miscible solvent that also is a solvent for the PHA, is added to the biomass slurry. The solvent addition should be made at a rate which approximates the rate of liquid permeation through the filter in order to maintain the volume of the biomass slurry. As the concentration of organic solvent in the slurry increases, various impurities which are insoluble in water become dissolved in the solvent-water mixture and pass through the filter membrane. When the organic solvent concentration reaches a certain level, the PHA becomes soluble and flows through the filtration membrane. The filtrate comprising PHA then is desolventized to recover the polymer.

Organic Solvents and Solvent Recovery

Solvents suitable for extracting the PHA from the biomass are any water miscible solvent capable of extracting the PHA. It is well known in the art which solvents are suitable for extracting the different PHA polymer compositions as described for example in U.S. Pat. Nos. 5,821,299 and 5,942,597 to Noda; U.S. Pat. No. 6,043,063 to Kurdikar; and PCT WO 97/15681 to Metabolix, Inc., all of which are incorporated herein by reference.

A preferred organic solvent for PHAs such as poly-3-hydroxyoctanoate (PHO) or other microbial polyesters comprising hydroxyacids from C6 to C14 in length is acetone. Acetone is also suitable for extracting poly-3-hydroxybutyrate-co-4-hydroxybutyrate. Other ketones and alcohols, especially alcohols above C2, can be used as described above. For PHO, solubilization of the polyester typically occurs at an acetone concentration from 85–48% in water (volume basis).

Organic solvents useful in the methods described herein include both halogentated and nonhalogentated solvents. Representative examples include solvents selected from cyclic and acyclic (linear and branched) R'—OH alcohols where R'=$C_4$-$Cl_{10}$, cyclic and acyclic R"—COOR'" esters where R"=H or $C_1$-$C_6$ and R'=$C_4$-$C_{10}$, cyclic and acyclic R"—COOR'" esters where R'=H or $C_1$-$C_6$ and R'''=$C_1$-$C_7$, and wherein at least one oxygen is substituted for at least one carbon in R" or R'", cyclic and acyclic $R^1$—CON—$(R^2)_2$ amides where $R^1$=H or $C_1$-$C_6$ and $R^2$=$C_1$-$C_6$, and cyclic and acyclic $R^3$—CO—$R^4$ ketones where $R^3$=$C_1$-$C_6$ and $R^4$=$C_1$-$C_6$.

Specific examples include acetone, butyl acetate, isobutyl acetate, ethyl lactate, isoamyl acetate, benzyl acetate, 2-methoxy ethyl acetate, tetrahydrofurfuryl acetate, propyl propionate, butyl propionate, pentyl propionate, butyl butyrate, isobutyl isobutyrate, ethyl butyrate, ethyl valerate, methyl valerate, benzyl benzoate, methyl benzoate, dimethyl succinate, dimethyl glutarate, dimethyl adipate, isobutyl alcohol, 1-butanol, 2-methyl-1-butanol, 3-methyl-1 butanol, 1-pentanol, 3-pentanol, amyl alcohol, allyl alcohol, hexanol, heptanol, octanol, cyclohexanol, 2-ethylhexanol, tetrahydrofurfuryl alcohol, furfuryl alcohol, benzyl alcohol, 2-furaldehyde, methyl isobutyl ketone, methyl ethyl ketone, g-butyrolactone, methyl n-amyl ketone, 5-methyl-2-hexanone, ethyl benzene, 1,3-dimethoxybenzene, cumene, benzaldehyde, 1,2-propanediol, 1,2-diaminopropane, ethylene glycol diethyl ether, 1,2,3-trimethylbenzene, 1,2,4-trimethylbenzene, 1,3-dioxane, 1,4-dioxane, 1-nitropropane, toluene-2,4-diisocyanate, acetic acid, acrylic acid, acetic anhydride, alpha-methylstyrene, acetophenone, toluene, ethylene glycol diacetate, dimethyl sulfoxide, dimethyl acetamide, dimethyl formamide and propylene carbonate.

Solvents which can be used include solvents or solvent mixtures including chloronated organic solvents such as chloroform, methylene chloride, dichloroethane, trichloroethane, tetrachloroethane and dichloroacetate. For example, hydrocarbon stabilized chloroform can be used. Other solvents which have been used to extract PHAs from microbial sources which may be used include alkyl carbonates, such as propylene carbonate and ethylene carbonate, trifluoroethanol, acetic anhydride, dimethylformamide, ethylacetoacetate, triolein, toluene, dioxane, tetrahydrofuran, diethylether, pyridine, hydroxyacids and alcohols having more than 3 carbon atoms, as well as mixtures thereof Solvent recovery can be carried out by processes well known to those skilled in the art and includes distillation or extraction into a second solvent or solvent mixture which is not miscible with water and subsequent separation by distillation Recovery of the PHA From the Eluant or Filtrate Once the polymer appears in the filtrate or eluant, it is necessary to recover the polymer from the solvent and also to recover the solvent.

Techniques for doing this are also well known in the art and include solvent stripping or evaporation, steam stripping or solvent precipitation with a non-solvent.

The compositions and methods described herein will be further understood with reference to the following non-limiting examples.

EXAMPLE 1

Typical Production of PHA-Containing Microbial Biomass

Pseudomonas species bacteria were fermented as follows to produce PHA. Octanoic acid (Prifrac 2901) was obtained from Unichema International, Chicago, Ill.; all other chemicals were reagent grade. Medium A contained deionized water plus the following (per L final volume): Octanoic acid (2.16 g), NaNH$_4$HP$_4$O (3.8 g), K$_2$HP$_4$O (5.7 g), KH$_2$PO$_4$ (3.7 g), MgSO$_4$ (0.12 g), CaCl$_2$ (20 mg), FeSO$_4$.7H$_2$O (40 mg), MnSO$_4$.H$_2$O (10 mg), CoCl$_2$.6H$_2$O (4.5 mg), ZnSO$_4$.7H$_2$O (2 mg), Na$_2$MoO$_4$.2H$_2$O (2 mg), CuCl$_2$.2H$_2$O (1mg), Al$_2$(SO$_4$)3.16H$_2$O (1.3 mg), H$_3$BO$_4$ (465 µg), NiSO$_4$.6H$_2$O (180 µg), corn steep liquor (Sigma, 0.5 mL). All components with the exception of octanoic acid were sterilized by heating (121.5° C.) or filtration and transferred aseptically into the vessel. The pH was adjusted to 6.7 and maintained throughout all fermentations at that value (±0.1 pH unit). Control of pH was effected using 30% (wt/wt) aqueous ammonia and 85% (wt/wt) phosphoric acid, which were added as needed via an automatic pH controller. Antifoam agent (Breox FMT30 obtained from Inspec Group, Southampton, UK) was added as needed during fermentations.

The culture was fed as described below with defined medium doses under metabolic ([DO]) control. Each defined medium dose consisted of three subdoses which were added simultaneously into the culture through separate addition ports. Subdose #1 consisted of octanoic acid (1.46 g per L initial culture volume); subdose #2 consisted of 30% (wt/wt) aqueous ammonia (0.36 g per L initial culture volume); subdose #3 consisted of 0.3MgSO$_4$ (0.4 mL per L initial culture volume). The time required to provide a single defined medium dose into the fermenter was approximately two minutes. Each defined medium dose provided sufficient nutrition to generate about 1.3 g/L total solids.

*Pseudomonas putida* was stored in frozen culture and propagated on 1.5% agar plates (Medium A). Frozen cultures were thawed, plated, and grown for 48 hr. at 30° C. Single colonies were then replated and grown for 24 hr. at 30° C. Single colonies were then chosen and transferred into liquid medium A (1 L) and grown in a shaker at 30° C. for 24 hr. This seed culture was then transferred into a 150 L fermenter containing defined Medium A (60 L) at 30° C. The fermenter was equipped with a single [DO] probe and pH probe. The culture was fermented at 30° C. with agitation (impeller speed 150–600 rpm) and aeration with atmospheric air (60 L/min) under a head pressure of 3 psi (20.7 MPa). Agitation rate was increased progressively through the course of the fermentation. Dissolved oxygen concentration was monitored continuously and a defined medium dose was provided in response to each sustained (>10 sec), significant (>10% saturation increase above prevailing baseline) increase in measured [DO]. During the first 8–9 hr. of fermentation, the [DO] dropped steadily from 100% to ca. 0% saturation. Thereafter the [DO] maintained a baseline condition of ca. 0% saturation. Agitation and aeration rates were controlled within these ranges to try to maintain [DO]=1% saturation. Sustained increases in the [DO] above 10% saturation were considered the result of carbon source exhaustion and triggered the automatic addition of a defined medium dose. Addition of each dose resulted in a decrease in [DO] back to the baseline condition. However, a feedback mechanism prevented multiple defined medium dose additions in case the [DO] were slow to return below 10% saturation. A total of 24 defined medium doses were provided over the course of the 21 hr. fermentation.

Immediately at the conclusion of the above fermentation, the culture was transferred aseptically into a 1500 L fermenter containing 640 L of defined Medium A. The fermenter was equipped with a single [DO] probe and pH probe, and a mass spectral off-gas analyzer. Fermentation was conducted under conditions similar to those above, with a temperature of 30° C., agitation (impeller speed 60–210 rpm), and aeration with atmospheric air (600–950 L/min) under a head pressure of 3 psi (20.7 MPa). After inoculation, [DO] dropped rapidly (within 3 hr.) to near 0% saturation. Agitation and aeration rates were controlled within the aforementioned ranges to try to maintain [DO]=1% saturation. The fermentation was continued for 41 hr.

The final culture consisted of 750 L containing 116.7 g/L of dry solids, of which 66.3% was PHA. The PHA had the following monomeric composition: R-3-hydroxyhexanoic acid (10%), R-3-hydroxyoctanoic acid (88%), R-3-hydroxydecanoic acid (2%). The isolated polymer showed $M_w$=115,000; $M_n$=70,000 (GPC in CHCl$_3$); $T_m$=50° C.; and $T_g$=−38° C.

EXAMPLE 2

Recovery of PHA from Microbial Biomass

A cell slurry containing polyhydroxyalkanoate (PHA) was processed as follows to obtain a purified polymer. Cells of Pseudomonas sp. bacteria were fermented as described in Example 1 on a commercial mixture comprising principally octanoic and decanoic acids (C810 Fatty Acid, Procter & Gamble, composition 56% C8, 39% C10, balance other fatty acids). The initial slurry (5 L), which comprised approximately 13% (wt/wt) suspended solids, was centrifuged at 4000 g for 20 min. The pellet fraction was resuspended to its original volume in deionized water and then recentrifuged under identical conditions. The pellet fraction was then resuspended in acetone to its original volume. This slurry comprising cellular material, water, and acetone (total solids=12.8% wt/wt) was then processed using the experimental apparatus described below.

The experimental microfiltration apparatus comprised an explosion proof, variable speed, eccentric screw pump (Allweiler) capable of at least 15 L/min flow against a head pressure of 0.6 MPa; a stainless steel and polypropylene piping circuit; and a housing containing an alumina ceramic tubular microfiltration element (U.S. Filter Membralox 1T1-70, 0.5 µm nominal cutoff, 0.0055 m$^2$ membrane area). In addition the apparatus was equipped with pressure gauges, temperature probes, a ball valve for pressure regulation, and a 20-L covered slurry tank. The liquid level in the slurry tank was maintained approximately constant through continuous addition of acetone via an adjustable feeding pump. During operation, the slurry was continuously circulated through the tubular ceramic membrane at a cross flow of approximately 15 L/min and an average transmembrane pressure of 0.3–0.6 MPa. Transmembrane flow rate ranged from 8–30 mL/min (90–330 L/m$^2$/hr). The system temperature was maintained at 20–32° C. by means of a glycol/water cooling jacket installed on the pump head. As the result of the continuous removal of permeate and continuous addition of pure acetone, the concentration of acetone in the slurry increased throughout the operation.

The acetone/water-comprising permeate was collected in a series of fractions. When the ratio of acetone to water in the slurry exceed a critical value of approximately 9:1 (wt/wt), the PHA copolymer became soluble and was passed through the ceramic membrane. The concentration of polymer in the permeate peaked at 5.8% wt/wt. The permeate was collected until the concentration of solids was <0.1% (wt/wt). Fractions containing PHA were combined (14 L), and the polymer was precipitated by addition of 10% (vol/vol) deionized water. The filter concentrate comprised acetone, water, and essentially PHA-free cell debris.

Modifications and variations of the present invention will be obvious to those of skill in the art from the foregoing detailed description. Such modifications and variations are intended to come within the scope of the following claims.

I claim:

1. A method for isolating and purifying polyhydroxyalkanoates (PHAs) derived from biomass comprising PHA, the method comprising
extracting PHA from the biomass using at least one solvent while simultaneously subjecting the biomass to a filtration process to remove cells.

2. The method of claim 1 wherein the filtration process comprises diafiltration.

3. The method of claim 2 wherein the diafiltration is conducted at a constant slurry volume.

4. The method of claim 1 wherein the biomass is subjected to a gradient in solvent concentration.

5. The method of claim 1 wherein the biomass is derived from a microbial source.

6. The method of claim 1 wherein the biomass is derived from a plant or plant part.

7. The method of claim 6 wherein the plant is an oilseed plant.

8. The method of claim 1 wherein the biomass is provided as an aqueous slurry and the solvent is an organic solvent.

9. The method of claim 8 wherein the organic solvent is acetone.

10. The method of claim 8 wherein the aqueous slurry and organic solvent form a solvent-water mixture, the method further comprising gradually increasing the concentration of organic solvent in the solvent-water mixture.

11. The method of claim 10 conducted in a diafiltration unit which comprises a filter membrane wherein the concentration of organic solvent is increased to cause impurities in the biomass which are insoluble in water to dissolve in the solvent-water mixture and pass through the filter membrane.

12. The method claim 11 wherein the concentration of organic solvent is increased to cause the PHA to dissolve in the solvent-water mixture and pass through the filter membrane to form a PHA filtrate.

13. The method of claim 12 further comprising removing the solvent from the PHA filtrate to recover the PHA.

* * * * *